United States Patent [19]

Yarovesky et al.

[11] Patent Number: 5,000,687
[45] Date of Patent: Mar. 19, 1991

[54] WINGED DENTAL BRIDGE AND PROCESS OF MANUFACTURING SAME

[76] Inventors: Uriel Yarovesky, 4144 Towhee Dr., Calabasas, Calif. 91302; Daniel Materdomini, 2700 Santa Maria Rd., Topanga Canyon, Calif. 90290

[21] Appl. No.: 510,977

[22] Filed: Apr. 19, 1990

[51] Int. Cl.$^5$ .............................................. A61C 13/225
[52] U.S. Cl. ..................................................... 433/180
[58] Field of Search ............... 433/180, 181, 191, 192, 433/215, 218

[56] References Cited

U.S. PATENT DOCUMENTS

| | | | |
|---|---|---|---|
| 4,479,527 | 10/1984 | Boettcher | 433/180 |
| 4,552,779 | 11/1985 | McClure | 433/191 |
| 4,957,439 | 9/1990 | Shoher et al. | 433/180 |

*Primary Examiner*—Cary E. Stone
*Attorney, Agent, or Firm*—Kelly, Bauersfeld & Lowry

[57] ABSTRACT

A winged dental bridge includes a flexible bridge framework which is attachable to two abutment teeth, and a relatively hard veneer for placement over an exposed labial surface of the bridge framework. The bridge framework includes a pontic, a first wing extending laterally outwardly therefrom for attachment to a first abutment tooth, and a second wing for attachment to a second abutment tooth. The bridge framework is formed of a laminated resinous composite material including an etchable material which forms the labial surface of the pontic and attachment surfaces of the wings, and a polishable material which entirely covers the lingual surface of the etchable material. In a method for making the winged dental bridge, the uncured resinous composite structure is applied over a separator to a cast taken of the patient's mouth. The uncured bridge framework is light cured on the bridge in a pressurized nitrogen gas environment, and subsequently heat and light cured. The pontic is contoured to receive a relatively hard veneer, a second cast is made of the first cast with the bridge framework applied, and the hard veneer is fabricated utilizing the second resultant cast. Prior to installation, all surface areas of the polishable resin are polished, and all surface areas of the etchable material are acid-etched. The wings of the bridge framework are cemented to the abutment teeth, and the veneer is fixed to the labial surface of the pontic utilizing a dental composite cement which can be colored to match the veneer color when applied to the pontic, to the color of the abutment teeth.

42 Claims, 4 Drawing Sheets

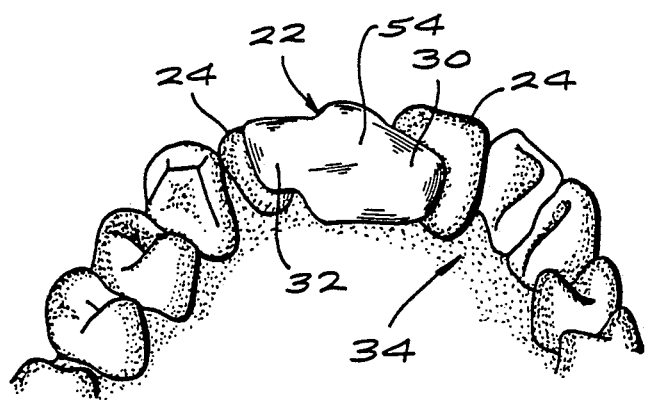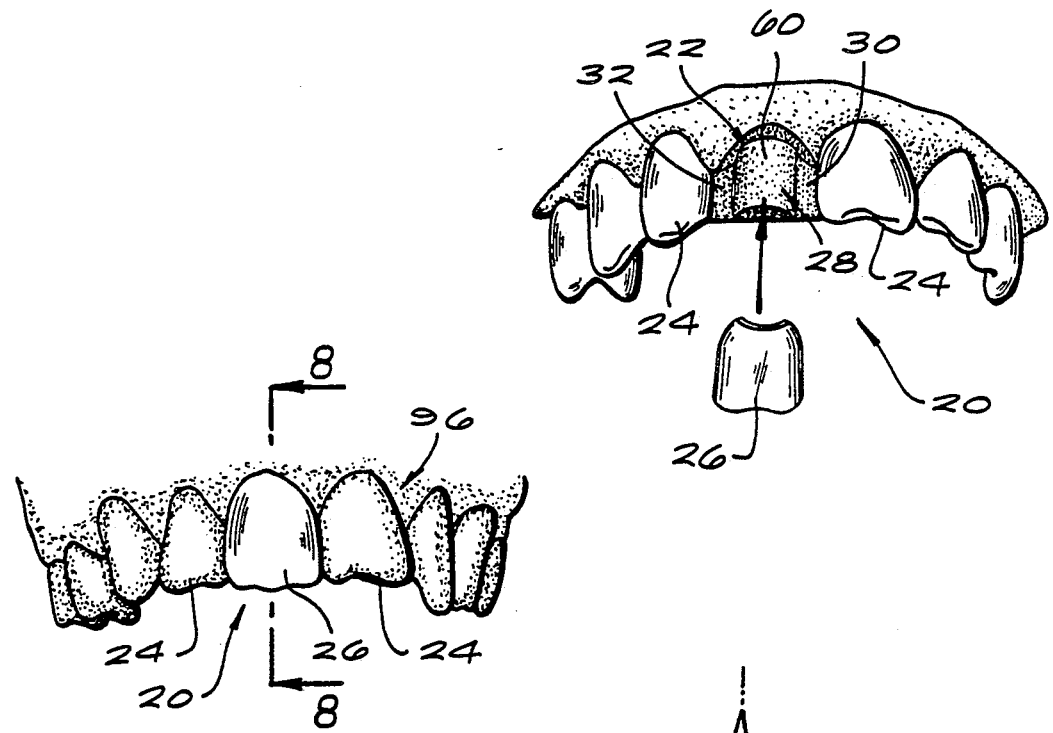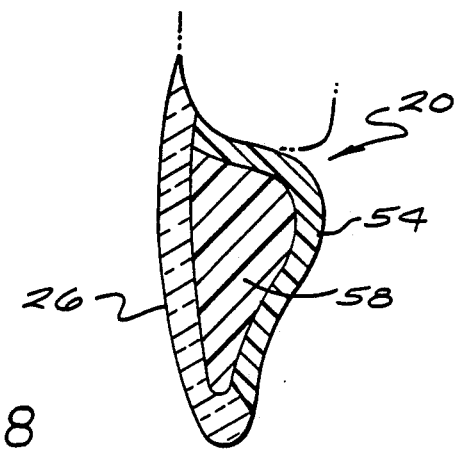

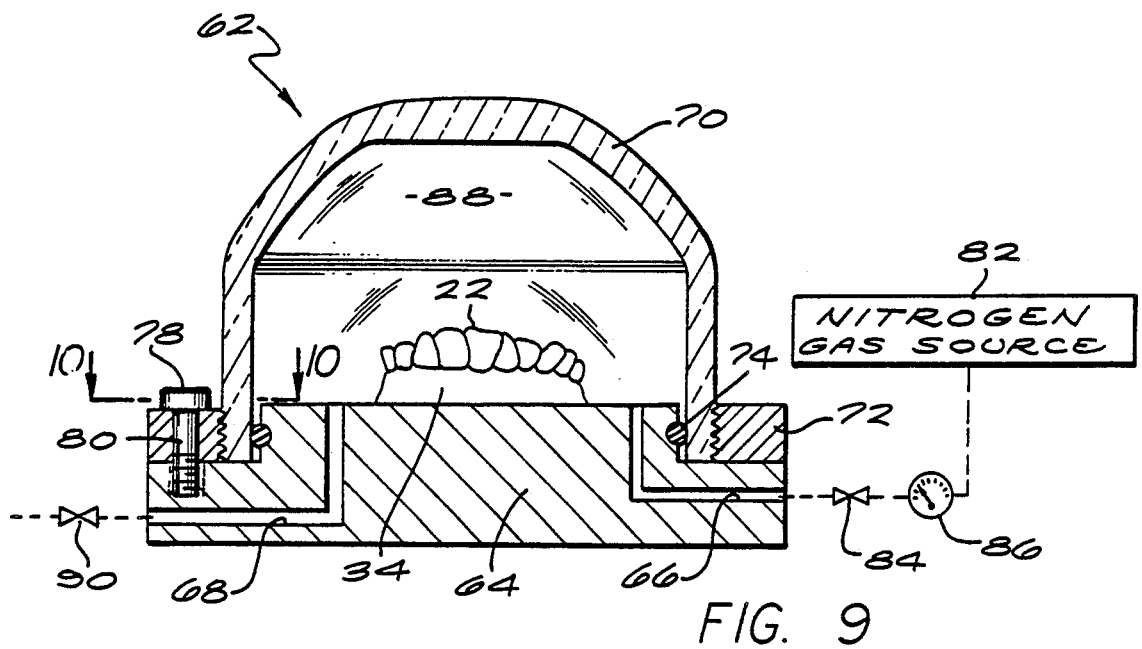
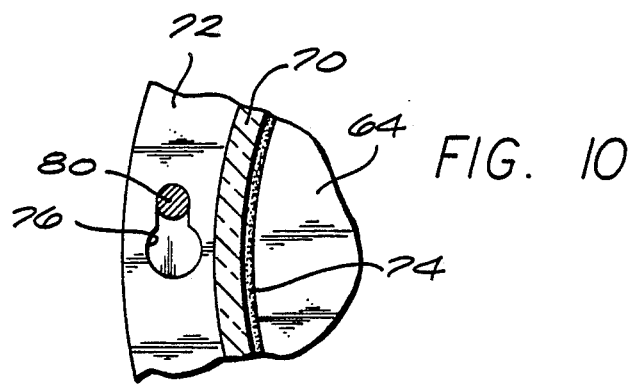
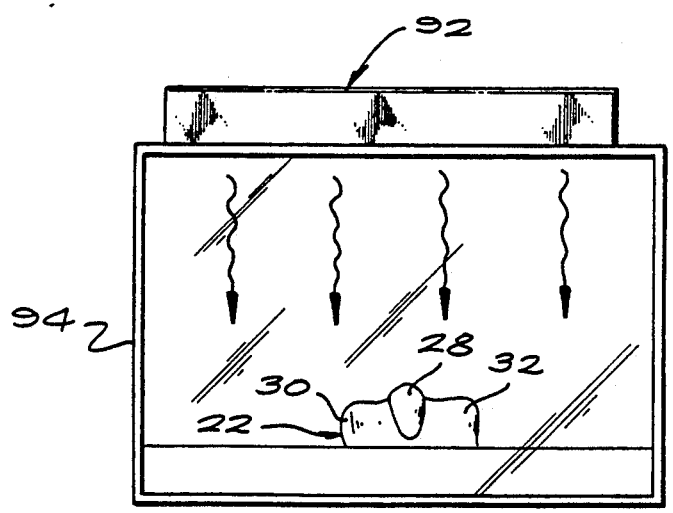

WINGED DENTAL BRIDGE AND PROCESS OF MANUFACTURING SAME

BACKGROUND OF THE INVENTION

This invention relates generally to dental bridges. More specifically, the present invention resides in a winged composite dental bridge for attachment to two or more abutment teeth, and a process for manufacturing the winged dental bridge and preparing the abutment teeth.

There has been a long-standing need in the dental art for a superior means for replacing a missing tooth. Many different types of dental bridges have been developed, but in recent years many dental professionals have shown a preference for resin bonded systems which can be utilized for the replacement of a single anterior tooth. Resin bonded systems have the advantage over other types of dental bridges in that preparation of the patient's mouth and existing teeth is minimal.

Some prior resin bonded systems, though conservative in nature, utilize a metallic bridge framework over which an enamel or porcelain is applied. In such systems there always exists the potential aesthetic disadvantage of mental "shine-through" at the incisal edge of the abutment teeth. Further, the prior systems typically have a fixed pontic color, which is frequently more opaque than desired.

In an effort to avoid the problems associated with the use of metals in a dental bridge, all-porcelain bridges have been developed which also require minimal tooth reduction. A problem associated with all-porcelain bridges is that they exhibit a higher incidence of porcelain fracture due to movement of the abutment teeth. This problem exists even when the teeth are just slightly mobile. Further, the all-porcelain bridge has a pontic color which is set during the manufacturing process, and which cannot be adjusted at the chair.

Accordingly, there has been a need for a novel dental bridge which integrates the strength and resiliency of a resinous bridge framework, with the aesthetic advantages of a porcelain-like veneer. Additionally, there exists a need for a novel dental bridge and process of manufacturing the same which requires conservative tooth preparation, which allows bridge flexure permitting class 1 mobility without fracture, and which utilizes non-metallic materials for optimum aesthetics and reduced risk of allergy. Further, a novel dental bridge and related method of manufacturer is needed which permits a two-phase placement technique in the mouth of a patient, thus eliminating pontic over-contouring, and gives chairside control to the dental professional over the final pontic shade. Moreover, a method of manufacturing such an improved dental bridge is needed which provides for maximum polymerization of the resinous bridge framework. Such a method should further provide for a high bond strength between the bridge framework and the abutment teeth, on the one hand, and a porcelain veneer on the labial surface of the pontic, on the other. The present invention fulfills these needs and provides other related advantages.

SUMMARY OF THE INVENTION

The present invention resides in an improved winged composite dental bridge for attachment to two abutment teeth, and a process for manufacturing the winged dental bridge. The dental bridge comprises, generally, a relatively flexible bridge framework which is fixed to the abutment teeth, and a relatively hard veneer which is subsequently fixed to the framework. The bridge framework includes a pontic and means attachable to the abutment teeth for supporting the pontic therebetween. The pontic is permitted limited flexure relative to the supporting means to give the bridge class 1 mobility without fracture.

In a preferred form of the invention, the means attachable to the abutment teeth for supporting the pontic therebetween includes a first wing which extends laterally outwardly from the pontic for attachment to a first abutment tooth, and a second wing which extends laterally outwardly from the pontic opposite to the first wing for attachment to a second abutment tooth. The bridge framework is formed of at least two laminated cured resin materials which, when manufactured in accordance with a preferred method, permit limited flexure of the pontic relative to the wings.

In accordance with a preferred process for manufacturing the winged dental bridge, the abutment teeth are first prepared to receive the dental bridge by cutting the lingual surfaces of the abutment teeth to form reduction or shaved areas. These shaved areas are contoured in a manner to receive the wings of the bridge framework and to facilitate a secure attachment between the wings and the abutment teeth. An impression is taken of the patient's mouth after the abutment teeth have been prepared, and a first cast is created from the impression. A separator is then applied to all surfaces of the cast which will come into contact with the dental bridge itself during subsequent manufacturing steps.

A resinous composite bridge framework is formed over the separator on the cast, which extends between the two abutment teeth. This is accomplished by applying a polishable resinous material to the saddle area of the cast, then applying an etchable resinous material to create the labial surface of the pontic and the attachment surfaces for the wings, and finally laminating a polishable resinous material to the etchable material, to entirely cover the lingual surface of the etchable material.

The uncured composite bridge framework is then light cured, while still mounted to the cast, in a pressurized nitrogen gas environment for seven minutes at a pressure of approximately 80 PSI. The partially cured bridge framework can then be removed from the cast and heat and light cured for an additional seven minutes at approximately 130° C. The pressurized nitrogen gas environment in which the uncured bridge framework is placed includes a chamber having a base on which the cast is positioned, and an overlying transparent dome which forms an air-tight chamber. A gas inlet passageway is provided through the base for pressurizing the chamber, and a separate air purge passageway insures that a pure nitrogen environment is attained.

After the bridge framework has been cured, the pontic portion is contoured to receive a porcelain-like veneer. The bridge framework is then secured to the first cast using sticky wax, an impression is taken, and a second cast is created. From this second cast, a relatively hard (porcelain) veneer is fabricated for placement over the labial surface of the bridge framework pontic.

Prior to installing a dental bridge in the mouth of the patient, the exposed surfaces of the etchable material, as well as the interior surfaces of the hard veneer, are acid-etched utilizing a hydroflouric acid. The exposed surfaces of the polishable material are polished. The dental bridge is then installed in the mouth of the patient by fixing the wings to the prepared abutment teeth, and subsequently attaching the hard veneer to the labial surface of the pontic. More particularly, the wings are fixed within the shaved areas of the abutment teeth by means of direct composite bonding. The hard veneer is attached to the labial surface of the bridge framework by utilizing a dental composite cement which is colored, if necessary, in order to match the color of the veneer when fixed to the pontic, to the color of the abutment teeth. This advantageously gives chairside control during the final installation step, over the final color of the normally visible portions of the winged dental bridge.

The use of nonmetallic components in the winged dental bridge of the present invention permits the manufacture of a bridge having sufficient hardness and aesthetic properties, while permitting some bridge flexure without fracture thereof. The nonmetallic materials reduce the risk of allergy, and the two phase placement technique eliminates pontic over contouring.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 5 is a lingual perspective view of the cast similar to FIG. 4, illustrating a next subsequent step in the manufacturing process which involves the laminating of a polishable resinous material to the etchable material, to entirely cover the lingual surface of the etchable material;

FIG. 6 is a labial perspective view of a patient's mouth showing a bridge framework affixed to the preparation areas of the abutment teeth, and showing the manner in which a porcelain veneer is fixed to the bridge framework to complete the winged dental bridge;

FIG. 7 is a labial perspective view similar to FIG. 6, illustrating the winged dental bridge as fully installed between the two abutment teeth;

FIG. 8 is an enlarged sectional view taken generally along the line 8—8 of FIG. 7, illustrating, specifically, the pontic area of the dental bridge, and the relationship of the cured composite materials to the porcelain veneer;

FIG. 9 is a sectional view of a pressure chamber utilized in light curing the resinous composite bridge framework;

FIG. 10 is an enlarged, fragmented and partially sectional plan view taken generally along the line 10—10 of FIG. 9, illustrating the manner in which a transparent dome is fixed to a base of the pressure chamber;

FIG. 11 illustrates a step in the curing process of the resinous composite bridge framework, wherein the bridge framework is removed from the cast after the light curing step, to be subsequently heat and light cured.

DETAILED DESCRIPTION OF THE PREFERRED EMBODIMENT

Figure 1:
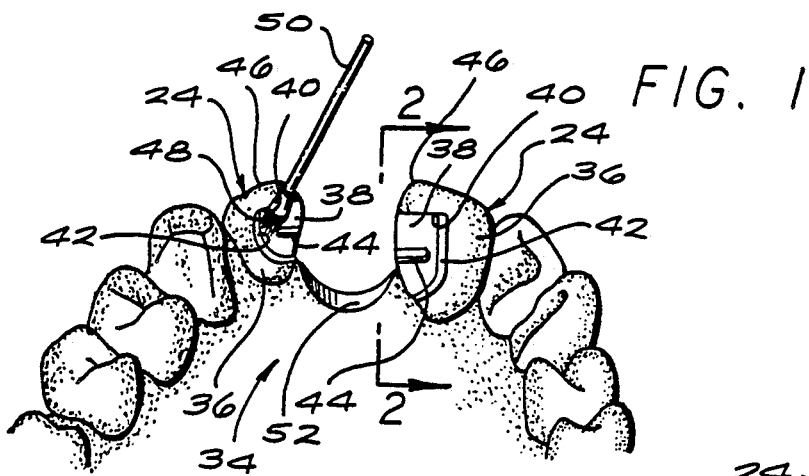
FIG. 1 is a perspective view of the lingual side of a cast, showing a missing tooth and two abutment teeth prepared prior to taking an impression for the cast, for receiving a winged dental bridge manufactured in accordance with the present invention, wherein the brush illustrates a step of applying a separator to the preparation areas of the cast.

As shown in the drawings for purposes of illustration, the present invention is concerned with an improved dental bridge, generally designated in the accompanying drawings by the reference number 20. The dental bridge 20 comprises, generally, a relatively flexible resin composite bridge framework 22 which is manufactured for attachment to a pair of abutment teeth 24, and a relatively hard (porcelain) veneer 26 which is attached at chairside to a pontic portion 28 of the bridge framework 22.

In accordance with the present invention, and as illustrated best in FIGS. 5 through 8 and 11, the bridge framework 22 includes the pontic portion 28, a first wing 30 extending laterally outwardly from the pontic 28 for attachment to a first abutment tooth, and a second wing 32 which extends laterally outwardly from the pontic opposite to the first wing for attachment to a second abutment tooth. The bridge framework 22 is formed of two laminated cured resinous materials which permit limited flexure of the pontic 28 relative to the wings 30 and 32.

Figure 12:
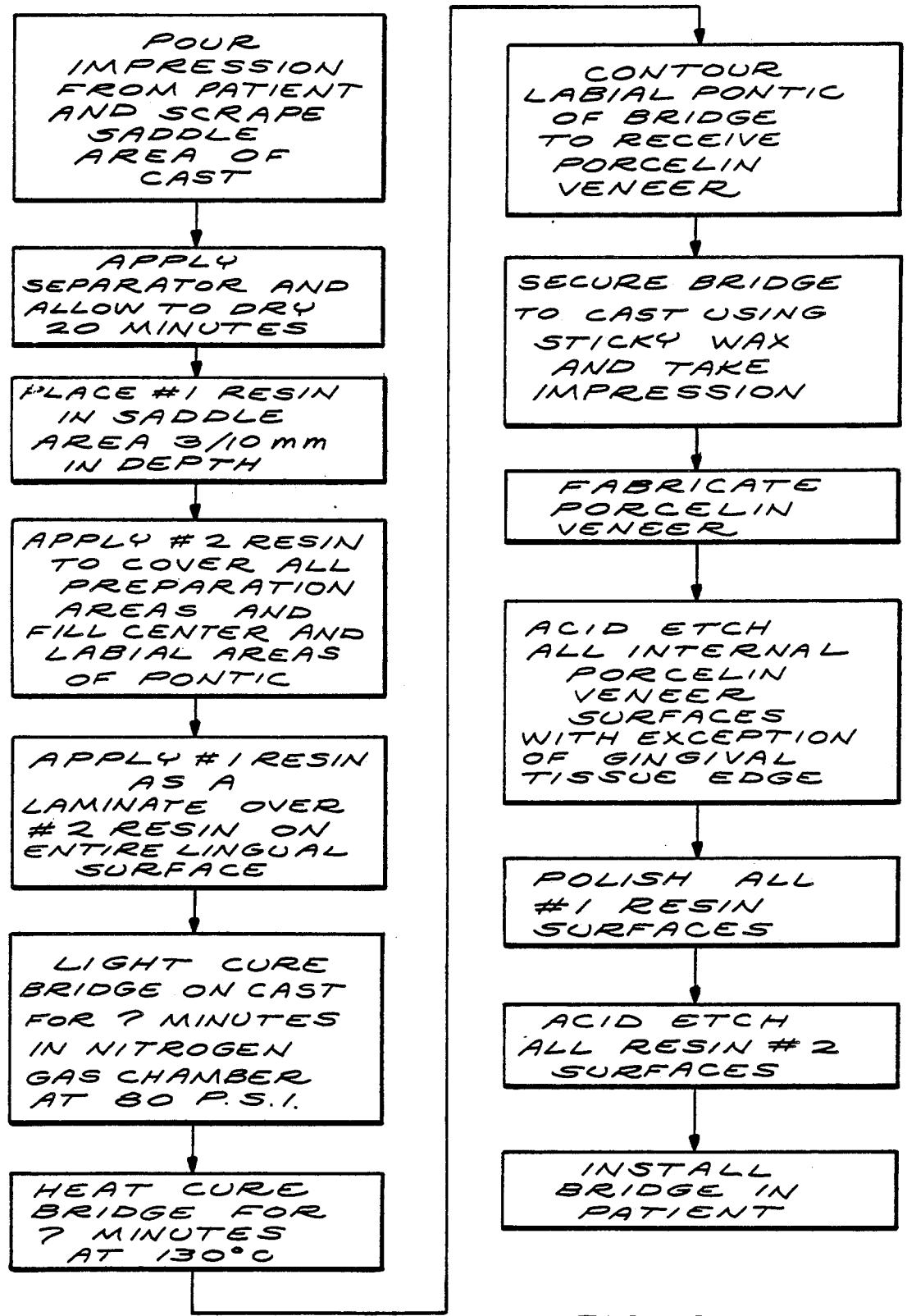
FIG. 12 is a logic diagram illustrating, generally, the process steps for manufacturing a winged dental bridge in accordance with the present invention.

The construction and characteristics of the winged dental bridge 20 will become more clear from the following discussion of a novel process for manufacturing the winged dental bridge and preparing the abutment teeth 24, which process is illustrated in logic diagram form in FIG. 12.

Figure 2:
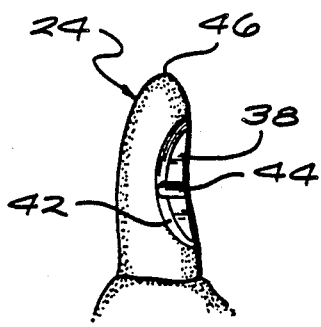
FIG. 2 is an enlarged elevational view of one abutment tooth taken generally along the line 2—2 of FIG. 1, illustrating the general contouring of a preparatory shaving of the abutment tooth.

Before taking an impression of the portion of a patient's mouth where the bridge 20 is to be installed, the abutment teeth 24 must first be prepared. With reference to FIGS. 1 and 2, which illustrate a cast 34 of a patient's mouth after the preparation has been accomplished, it will be seen that preparation of the abutment teeth 24 involves the cutting of the lingual surfaces 36 to form reduced or shaved areas 38 which are contoured and dimensioned to receive the wings 30 and 32 of the bridge framework 22. Tooth preparation for the winged dental bridge 20 is predominantly a lingual surface preparation with a slight proximal extension. The basic outline form resembles a half-watermelon and encompasses appoximately one-half of the lingual surface 36 of each abutment tooth 24 from the mesiolingual transition angle to the distolingual transition angle.

A 379-023F diamond burr (watermelon shaped burr from Brasseler) is used to create two separate cuts which are blended to produce sufficient bulk for the wings 30 and 32 of the bridge framework 22. Mesiodistally (horizontally), the first preparation cut border 40 is preferably one-half the distance from the proximal wall of the tooth. This may be slightly more than one half the distance, but never more than two-thirds of the distance for narrow teeth. Cervicoincisally (vertically), the first preparation cut border 40 is about 1 mm from the incisal edge of the abutment tooth 24, and about 1 mm from the gingival papilla tip (or the cementoenamel junction, whichever comes first) at the greatest length of the preparation at the linguolproximal line angle. Proximally, at the pontic connector site in the middle to incisal one-third of the tooth 24, the second preparation cut border 42 is never more than one-third of the distance from the lingual proximal angle to the facloproximal line angle. From this theory of maximum proximal extension, the proximal outline forms a relatively flat arch to connect with the lingual preparation cut border, where it is 1 mm from the incisal edge and 1 mm from the gingival papilla tip. The two tooth preparation cuts 40 and 42 merge to form a relatively sharp line angle. This line angle is flattened, without creating a deep penetration, thereby blending the lingual and proximal preparation cuts into a smooth continuous surface.

To increase general retention and resistance form, a horizontal groove 44 about 0.5 mm in depth is made with an 855-041M diamond burr (in Nixon PVII kit from Brasseler). This burr is a sub-nosed diamond burr with a 1 mm cross-section diameter at the top and is designed to create a relatively conservative groove 44. The groove 44 should be placed approximately midway between the most incisal and most cervical extension of the preparation on the lingual surface 36. It should run parallel from the incisal edge 46 of the tooth and begin about 0.5 mm from the midlingual termination of the finish line. It should run horizontally and conclude approximately at the most proximal extension of the finish line.

Figure 3:
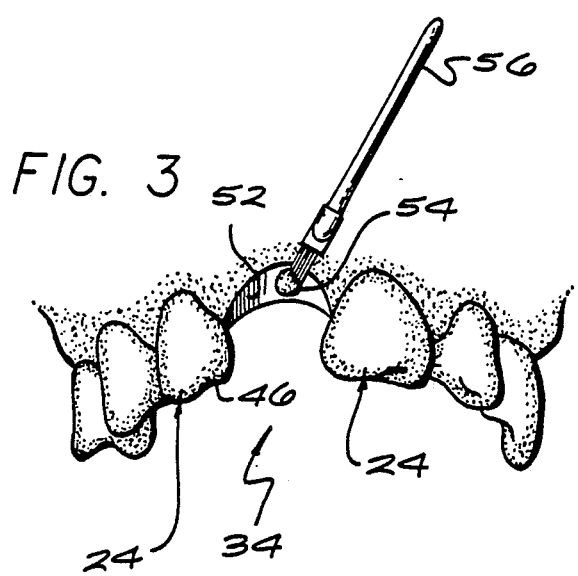
FIG. 3 is a labial perspective view of the cast illustrated in FIG. 1, showing a next sequential step in the process of manufacturing the winged dental bridge of the present invention, involving the application of a polishable resin over the separator in a saddle area of the cast.

Following preparation of the lingual surfaces 36 of the abutment teeth 24, an impression is taken of the patient's mouth and a first cast 34 is created utilizing standard techniques. The resultant cast structure is illustrated in FIGS. 1 through 3. Before fabrication of the dental bridge 20 is begun in connection with the cast 34, the tissue areas on the cast are trimmed so that all margins are visible. Preferably, these margins are outlined using an indelible pencil. A saddle area 52 is scraped with a knife approximately three pencil scrapings, and any undercuts are blocked out.

Next, a separator 48 is applied by means of a brush 50 to all surfaces of the cast 34 which are likely to come into contact with the bridge framework 22. These areas include the saddle area 52 and all shaved areas 38 on the lingual surfaces 36 of the abutment teeth 24. Preferably, the separator is a silicone or latex based, semi-tranparent separator which has been thinned to leave a very thin layer of separator only on the cast 34. Use of a lacquer thinner to thin the separator has been found to be acceptable. After the separator 48 is applied to the cast 34, it is allowed to dry approximately twenty minutes.

Following application of the separator 48 to the cast 34, a flexible, translucent, highly polishable resin (resin #1) 54 is placed over the separator 48 in the saddle area 52 of the cast 34. The resin 54 is applied by means of a brush 56 to a depth of approximately 0.3 mm. The #1 resin 54 is a highly filled microfill resin comprising, in approximate percentages, 24% acid-etched, semiporous glass filler, 47% submicron (0.04 u) silica, 22% Bis-GMA-E, 6% Diluent Monomer, 0.2% CQ, and 0.7% Amine. This composite is a highly filled, light and heat curable highbred composite which, when cured, has characteristics of high strength, resiliency and a highly polishable smooth surface.

Figure 4:
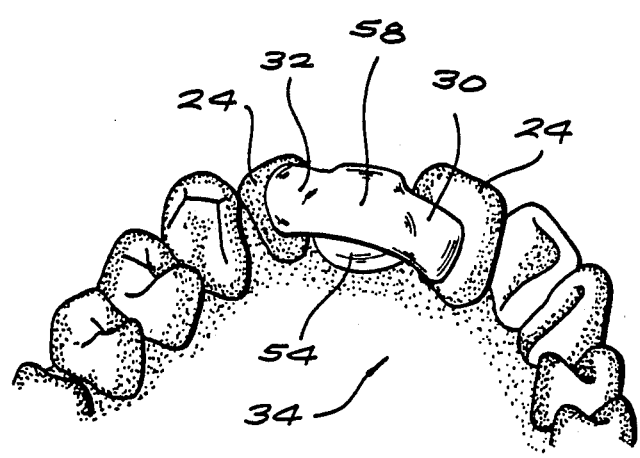
FIG. 4 is a lingual perspective view of the cast similar to that illustrated in FIG. 1, showing a subsequent step in the process of manufacturing the winged dental bridge, involving the application of an etchable composite resin material to the cast to create the labial surface of a pontic and attachment surfaces for a pair of wings.

After the #1 resin 54 is applied to the saddle area 52, a #2 resin 58, which is acid-etchable, is applied to the cast to create a labial surface and body of the pontic portion 28 of the bridge framework 22, and attachment surfaces for the wings 30 and 32 (FIG. 4). The etchable resin 58 may overlie a portion of the polishable resin 54 previously applied to the saddle area 52, and a sufficient amount of the etchable resin (#2 resin) 58 is applied to cover all of the preparation areas of the cast 34 and fill the center of the pontic portion 28. Preferably, the etchable resin is a composite comprising, in approximate percentages, 44% acid-etched, semiporous glass filler, 35% submicron (0.04 u) silica, 16% Bis-GMA, 5% diluent monomer, 0.05% CQ, 0.5% amine and 0.4 percent hydroperoxide. Both the #1 and #2 resins are manufactured by BISCO, Inc. of Downers Grove, Ill.

Next, the polishable resin 54 (#1 resin) is applied as a laminate over the etchable resin 58 (#2 resin), to entirely cover the lingual surface of the etchable resin 58 (FIG. 5). With the polishable and etchable resins 54 and 58 applied as described to the cast 34, the basis for the bridge framework 22 has been formed, but it exists in an uncured state. The polishable resin (#1 resin) 54 preferably has a depth of approximately 0.3 mm.

The next step in the process for preparing the novel winged dental bridge 20 is to cure the composite bridge framework 22, wherein at least a portion of the curing of the bridge framework is accomplished with the bridge framework mounted to the cast 34. For this purpose, as illustrated best in FIGS. 9 and 10, the cast with the uncured bridge framework 22 applied is placed within a pressurized chamber apparatus 62. This pressurized chamber apparatus 62 includes a base 64 having an inlet fluid passageway 66 and an outlet fluid passageway 68. Overlying the base 64 is a transparent dome 70 which is threaded, at its lower end, to a retention flange 72. An O-ring 74 is interposed between the base 64 and a lower portion of the dome 70 to form an air-tight seal between the base and the dome.

The retention flange 72 includes a plurality of keyways 76 which are dimensioned to pass over the heads 78 of bolts 80 secured in the base 64, in order the lock the dome 70 in place onto the base 64. The inlet fluid passageway 66 is connected to a nitrogen gas source 82, and a valve 84 and a pressure gauge 86 are provided in the line between the base 64 and the nitrogen gas source 82, in order to allow a user to monitor and control the introduction of nitrogen into a chamber 88 defined between the base and the dome. Further, an outlet valve 90 is provided adjacent to the outlet fluid passageway 68, to provide a means for purging air within the chamber 88.

The uncured bridge framework 22 applied to the cast 34 is placed within the chamber 88 for purposes of an initial cure of the resin composite materials. Both the inlet and outlet valves 84 and 90 are opened, and nitrogen from the nitrogen gas source 82 is injected into the chamber 88. Once the air originally in the chamber 88 has been purged, the outlet valve 90 is closed, and the chamber 88 is pressurized with nitrogen gas to approximately 80 PSI. The bridge framework 22 is illuminated with white light through the dome 70 to effect a light cure of the bridge framework 22 as applied to the cast 34, for seven minutes in the pressurized nitrogen environment.

Following this initial light/pressure curing step, the partially cured bridge framework 22 is removed from the cast 34 and placed within an oven 92 to further cure the bridge framework under heat for seven minutes at approximately 130° C. Preferably, the oven 92 is provided with tranparent walls 94 which permit observation of the curing bridge framework 22, and also permit the bridge framework to be illuminated with white light for further light curing thereof.

After the bridge framework 22 has been cured as described, the labial surface 60 of the pontic 28 is contoured in a standard manner to receive the veneer 26. The contour is shown generally in FIG. 6. The bridge framework 22 is secured to the cast 34 using a sticky wax, and then an impression is taken of the cast 34 and the bridge framework 22. A second cast 96 is then made, and a porcelain veneer is fabricated, utilizing standard techniques, for application to the pontic 28 of the bridge framework 22. The porcelain veneer 26 provides a rigid and aesthetically pleasing outer surface for the dental bridge 20 in the pontic area, and is preferably designed to provide a hard bite surface.

With fabrication of the veneer 26 complete, the internal surfaces of the veneer are etched utilizing a hydroflouric acid. Similarly, all of the areas of the bridge framework 22 to be bonded to either the veneer 26 or the abutment teeth 24 are also acid-etched with a hydroflouric acid. The acid agent used is a 7% gel agent which is applied for thirty seconds and then brushed off using water. On the bridge framework 22, those portions to be attached to the veneer 26 or the abutment teeth 24 generally comprise the exposed surfaces of the etchable resin 58 (#2 resin). Before installing the bridge 20, the surface areas of the polishable resin 54 are all polished to provide a smooth lingual surface for the dental bridge 20, as well as a smooth surface between the bridge and adjacent gingival tissue. A cross-section of the pontic is illustrated in FIG. 8.

Following completion of the above-listed manufacturing process steps, the winged dental bridge 20 is ready for installation into the mouth of the patient. This is accomplished by affixing the wings 30 and 32 of the bridge framework 22 to the shaved areas 38 on the lingual surfaces of the abutment teeth 24, by bonding the labial, etched surfaces of the wings directly to the prepared abutment teeth. Once the bridge framework 22 has been secured in place between the abutment teeth 24, the hard (porcelain) veneer is then attached to the labial surface of the pontic 28 of the bridge framework 22. A dental composite resin cement such as found in the INSURE resin cement kit by Cosmodent, is preferably utilized in attaching the veneer 26 to the pontic portion 28. The dental composite resin cement may be colored, if necessary, by the dental professional during installation in order to match the final color of the veneer when fixed to the pontic, to the color of the abutment teeth 24. This provides a significant advantage over prior dental bridges, by permitting the dental professional to fine tune the final color of the dental bridge at chairside.

From the foregoing it should be appreciated that the improved winged dental bridge 20 of the present invention incorporates the advantages of a flexible composite bridge framework with the superior aesthetics of a hard porcelain veneer for the replacement of an anterior tooth. The bridge framework 22 is capable of withstanding class 1 mobility without fracture. This is accomplished, at least in part, through the unique process of heat, light and pressure curing of the composite resin materials. Since no metal is used, there is no compromise of aesthetics due to "shine-through." The two-phase placement technique eliminates pontic over contouring, permits conservative tooth preparation and allows chairside control of the pontic shade. Bonding of the bridge framework and the veneer is accomplished utilizing conventional light-cured resins. In some cases, the procedure does not require anesthesia and is accomplished in substantially less time at chairside than other crown and bridge procedures.

Although a particular embodiment of the invention has been described in detail for purposes of illustration, various modifications may be made without departing from the spirit and scope of the invention. Accordingly, the invention is not to be limited, except as by the appended claims.

We claim:

1. A winged dental bridge for attachment to two abutment teeth, the bridge comprising:
 a bridge framework including a pontic, a first wing extending laterally outwardly from the pontic for attachment to a first abutment tooth, and a second wing extending laterally outwardly from the pontic opposite to the first wing for attachment to a second abutment tooth, the bridge framework being formed of at least two laminated cured resinous materials to permit limited flexure of the pontic relative to the wings; and
 a porcelain-like veneer fixed to a labial surface of the pontic.

2. A dental bridge as set forth in claim 1, wherein a second of the at least two laminated cured resinous materials forms the labial surface of the pontic and attachment surfaces for the wings adjacent to the abutment teeth.

3. A dental bridge as set forth in claim 2, wherein a second cured resinous material is acid-etchable.

4. A dental bridge as set forth in claim 3, wherein the labial surface of the pontic and the attachment surfaces of the wings are acid-etched.

5. A dental bridge as set forth in claim 2, wherein a first of the at least two laminated cured resinous materials is laminated to entirely cover a lingual surface of the second cured resinous material.

6. A dental bridge as set forth in claim 5, wherein the first cured resinous material is highly polishable, and wherein all lingual surfaces of the first cured resinous material are polished.

7. A dental bridge as set forth in claim 5, wherein the first cured resinous material is laminated to the second cured resinous material to be interposed between gingival tissue and the second cured resinous material.

8. A dental bridge as set forth in claim 1, wherein the veneer provides a hard bite surface to the bridge and is attached to the pontic such that the veneer is permitted limited flexure relative to the wings.

9. A dental bridge as set forth in claim 8, wherein the internal surfaces of the veneer are acid-etched, with the exception of a gingival tissue edge, and the veneer is fixed to the pontic by a dental cement.

10. A composite dental bridge for attachment between two abutment teeth, the bridge comprising:
a bridge framework including a pontic and means attachable to the abutment teeth for supporting the pontic therebetween, the bridge framework having a first primary structure forming a labial surface of the pontic and an attachment surface for the supporting means, and a second primary structure laminated to a lingual surface of the first primary structure, wherein the pontic is permitted limited flexure relative to the supporting means; and
a porcelain-like veneer fixed to the labial surface of the pontic.

11. A dental bridge as set forth in claim 10, wherein the internal surfaces of the veneer are acid-etched, with the exception of a gingival tissue edge, and the veneer is fixed to the pontic by a dental cement to provide a hard bite surface to the bridge.

12. A dental bridge as set forth in claim 10, wherein the first primary structure comprises an etchable cured resinous material, and wherein the labial surface of the pontic and the attachment surface for the supporting means are etched.

13. A dental bridge as set forth in claim 10, wherein the second primary structure comprises a polishable cured resinous material which is laminated to the etchable material to entirely cover the lingual surface of the first primary structure.

14. A dental bridge as set forth in claim 13, wherein the second primary structure is laminated to the first primary structure to be interposed between gingival tissue and the first primary structure, and wherein all lingual surfaces of the second primary structure are polished.

15. A dental bridge as set forth in claim 10, wherein the supporting means includes a first wing extending laterally outwardly from the pontic for attachment to a first abutment tooth, and a second wing extending laterally outwardly from the pontic opposite to the first wing for attachment to a second abutment tooth.

16. A winged composite dental bridge for permanent attachment to two abutment teeth, the bridge comprising:
a bridge framework including a pontic, a first wing extending laterally outwardly from the pontic for attachment to a first abutment tooth, a second wing extending laterally outwardly from the pontic opposite to the first wing for attachment to a second abutment tooth, the bridge framework being formed of at least two laminated cured resinous materials to permit limited flexure of the pontic relative to the wings, wherein one of the at least two materials comprises an etchable cured resinous material which forms a labial surface of the pontic and attachment surfaces for the wings adjacent to the abutment teeth, and wherein another of the at least two materials comprises a polishable cured resinous material which is laminated to the etchable material to entirely cover a lingual surface of the etchable material; and
a porcelain-like veneer fixed to a labial surface of the pontic, wherein the veneer is fixed to the pontic by a dental cement to provide a hard bite surface to the bridge.

17. A dental bridge as set forth in claim 16, wherein the labial surface of the pontic and the attachment surfaces for the wings are acid-etched, wherein all lingual surfaces of the bridge framework are polished, and wherein the internal surfaces of the veneer are acid-etched.

18. A process for manufacturing a dental bridge for attachment between two abutment teeth, the steps comprising:
preparing the abutment teeth to receive the dental bridge;
creating a first cast of a portion of a patient's mouth including the prepared abutment teeth;
applying a separator to surfaces of the cast to come into contact with the bridge;
forming a resinous composite bridge framework over the separator which extends between the two abutment teeth, such that the bridge framework includes a pontic, a first wing extending laterally outwardly from the pontic for attachment to a first abutment tooth, and a second wing extending laterally outwardly from the pontic opposite to the first wing for attachment to a second abutment tooth, wherein the forming step includes the steps of applying an etchable resinous material to the cast to create the labial surface of the pontic and the attachment surfaces for the wings, and laminating a polishable resinous material to the etchable material, to entirely cover the lingual surface of the etchable material;
curing the composite bridge framework, wherein at least a portion of the curing of the bridge framework is accomplished with the bridge framework mounted to the cast;
contouring the pontic to receive a porcelain-like veneer;
creating a second cast of the first cast having the bridge framework secured thereto;
fabricating a relatively hard veneer for placement over the labial surface of the pontic, utilizing the second cast; and
installing the dental bridge in the mouth of the patient by fixing the wings to the prepared abutment teeth, and attaching the hard veneer to the labial surface of the pontic.

19. A process as set forth in claim 18, wherein the step of preparing the abutment teeth includes cutting the lingual surfaces of the abutment teeth to form shaved areas on such surfaces to receive the wings of the bridge framework.

20. A process as set forth in claim 18, wherein the step of applying a separator includes the step of providing a latex separator and thinning the separator prior to its application to the cast with a lacquer thinner.

21. A process as set forth in claim 18, wherein the step of forming the resinous composite bridge framework includes the step of applying a polishable resinous material between the etchable material and portions of the cast representing gingival tissue.

22. A process as set forth in claim 18, wherein the step of curing the composite bridge framework includes the step of light curing the bridge framework in a pressurized nitrogen gas environment, and then heat curing the bridge framework.

23. A process as set forth in claim 22, wherein the bridge framework is light cured on the cast for seven minutes in a nitrogen gas chamber at approximately 80 PSI.

24. A process as set forth in claim 23, wherein the gas chamber includes a base on which the cast is positioned, an overlying transparent dome which forms an air-tight chamber, a gas inlet passageway through the base, and a separate air purge passageway through the base.

25. A process as set forth in claim 22, wherein bridge framework is heat cured for seven minutes at approximately 130° C.

26. A process as set forth in claim 18, wherein the step of fixing the wings to the prepared abutment teeth includes cementing the labial surfaces of the wings directly to the prepared abutment teeth.

27. A process as set forth in claim 18, wherein the step of attaching the hard veneer to the labial surface of the pontic includes the step of utilizing a dental composite cement which is colored, if necessary, to match the color of the veneer when fixed to the pontic, to the color of the abutment teeth.

28. A process as set forth in claim 18, including the step of acid-etching exposed surfaces of the etchable material of the bridge framework prior to the step of installing the dental bridge in the mouth.

29. A process as set forth in claim 28, wherein the etching step is accomplished utilizing a hydroflouric acid.

30. A process as set forth in claim 18, including the step of polishing the exposed surfaces of the polishable material of the bridge framework prior to the step of installing the dental bridge in the mouth.

31. A process as set forth in claim 18, including the step of acid etching internal surfaces of the hard veneer prior to the step of attaching the hard veneer to the labial surface of the pontic.

32. A process for manufacturing a winged dental bridge, the steps comprising:
 creating a cast of the portion of a patient's mouth where the bridge is to be installed;
 applying a separator to surfaces of the cast to come into contact with the bridge;
 forming a resinous composite bridge framework over the separator which extends between two abutment teeth, wherein the bridge framework includes a pontic and means attachable to the abutment teeth for supporting the pontic therebetween such that the pontic, when cured, is permitted limited flexure relative to the supporting means;
 curing the composite bridge framework, wherein at least a portion of the curing of the bridge framework is accomplished with the bridge framework mounted to the cast;
 fabricating a relatively hard veneer for placement over a labial surface of the pontic; and
 attaching the hard veneer to the labial surface of the pontic.

33. A process as set forth in claim 32, including the step of preparing the abutment teeth to receive the dental bridge, wherein the abutment teeth preparation step includes cutting of the lingual surfaces of the abutment teeth to form shaved areas for receiving the means attachable to the abutment teeth of the composite bridge framework.

34. A process as set forth in claim 32, wherein the step of applying a separator includes the step of providing a thinned latex separator.

35. A process as set forth in claim 32, wherein the means attachable to the abutment teeth for supporting the pontic therebetween includes a first wing extending laterally outwardly from the pontic for attachment to a first abutment tooth, and a second wing extending laterally outwardly from the pontic opposite to the first wing for attachment to a second abutment tooth, wherein the forming step includes the steps of applying an etchable resinous material to the cast to create the labial surface of the pontic and the attachment surfaces for the wings, and laminating a polishable resinous material to the etchable material to entirely cover the lingual surface of the etchable material.

36. A process as set forth in claim 35, including the steps of acid-etching exposed surfaces of the etchable material, polishing the exposed surfaces of the polishable material of the bridge framework, and acid-etching the internal surfaces of the hard veneer.

37. A process as set forth in claim 32, wherein the step of curing the composite bridge framework includes the step of light curing the bridge framework in a pressurized nitrogen gas environment.

38. A process as set forth in claim 37, wherein the step of curing the composite bridge framework further includes the steps of light curing the bridge framework on the cast for seven minutes in a nitrogen gas chamber pressurized to approximately 80 PSI, and heat curing the bridge framework for seven minutes at approximately 130° C.

39. A process as set forth in claim 38, wherein the nitrogen gas is pressurized within a gas chamber having a base on which the cast is positioned, an overlying transparent dome which forms an air-tight chamber, a gas inlet passageway through the base, and a separate air purge passageway through the base.

40. A process as set forth in claim 32, wherein the step of attaching the hard veneer to the labial surface of the pontic includes the step of utilizing a dental composite cement which is colored, if necessary, to match the color of the veneer when fixed to the pontic, to the color of the abutment teeth.

41. A process for manufacturing a winged dental bridge and preparing abutment teeth to which the dental bridge will be attached, the steps comprising:
 preparing the abutment teeth to receive the dental bridge, the preparing step including the cutting of the lingual surfaces of the abutment teeth to form shaved preparation areas;
 creating a first cast of the portion of a patient's mouth including the prepared abutment teeth;
 applying a separator to all surfaces of the cast to come into contact with the bridge;
 forming a resinous composite bridge framework over the separator and extending between the abutment teeth, wherein the bridge framework includes a pontic and means attachable to the abutment teeth for supporting the pontic therebetween such that a pontic is permitted limited flexure relative to the supporting means, the means attachable to the abutment teeth for supporting the pontic therebetween including a first wing extending laterally outwardly from the pontic for attachment to a first abutment tooth, and a second wing extending laterally outwardly from the pontic opposite to the first wing for attachment to a second abutment tooth, wherein the forming step includes the steps of applying an etchable resinous material to the cast to create the labial surface of the pontic and the attachment surfaces for the wings, laminating a polishable resinous material to the etchable material to entirely cover the lingual surface of the etchable material, and applying a polishable resinous material between the etchable material and portions of the cast representing gingival tissue;

curing the composite bridge framework, wherein at least a portion of the curing of the bridge framework is accomplished with the bridge framework mounted to the cast, wherein the curing step includes the steps of light curing the bridge framework in a pressurized nitrogen gas environment, and heat curing the bridge framework;

contouring the pontic to receive a porcelain-like veneer;

creating a second cast of the first cast having the bridge framework secured thereto;

fabricating a relatively hard veneer for placement over the labial surface of the pontic, utilizing the second cast; and preparing surfaces of the bridge framework and the hard veneer by acid-etching exposed surfaces of the etchable material and the internal surfaces of the hard veneer, and polishing the exposed surfaces of the polishable material.

42. A process as set forth in claim 41, wherein the step of curing the composite bridge framework includes the steps of placing the cast with the uncured bridge framework attached thereto into a gas chamber having a base on which the cast is positioned, an overlying transparent dome which, with the base, forms an air-tight chamber, and an inlet passageway through the base, light curing the cast for seven minutes in a nitrogen environment at approximately 80 PSI, and then heat curing the bridge framework for seven minutes at appoximately 130° C.

* * * * *